United States Patent [19]

Neubauer et al.

[11] Patent Number: 5,120,756
[45] Date of Patent: Jun. 9, 1992

[54] SUBSTITUTED N-HYDROXYPYRAZOLES AND N-HYDROXY-TRIAZOLES FOR CONTROLLING PESTS

[75] Inventors: Hans-Juergen Neubauer, Muenster-Hiltrup; Uwe Kardoff, Mannheim; Joachim Leyendecker, Ladenburg; Ulf Baus, Dossenheim; Christoph Kuenast, Otterstadt; Peter Hofmeister, Neustadt; Wolfgang Krieg, Weingarten; Reinhard Kirstgen, Neustadt; Wolfgang Reuther, Heidelberg-Ziegelhausen, all of Fed. Rep. of Germany

[73] Assignee: BASF Aktiengesellschaft, Ludwigshafen, Fed. Rep. of Germany

[21] Appl. No.: 638,011

[22] Filed: Jan. 7, 1991

Related U.S. Application Data

[63] Continuation of Ser. No. 482,909, Feb. 22, 1990, abandoned.

[30] Foreign Application Priority Data

Mar. 3, 1989 [DE] Fed. Rep. of Germany ....... 3906772
Dec. 14, 1989 [DE] Fed. Rep. of Germany ....... 3941296

[51] Int. Cl.⁵ .................. A01N 43/56; C07D 231/10
[52] U.S. Cl. .................. 514/407; 548/375; 548/376
[58] Field of Search .............. 548/375, 376; 514/407

[56] References Cited

U.S. PATENT DOCUMENTS 4,764,527 8/1988 Wagner et al. ............. 514/407
4,943,586 7/1990 Bowers et al. ............. 548/375

FOREIGN PATENT DOCUMENTS 0289919 11/1988 European Pat. Off.
2115812 9/1983 United Kingdom.

Primary Examiner—Patricia L. Morris
Attorney, Agent, or Firm—Keil & Weinkauf

[57] ABSTRACT

Novel substituted N-hydroxypyrazoles or N-hydroxytriazoles of the general formula I

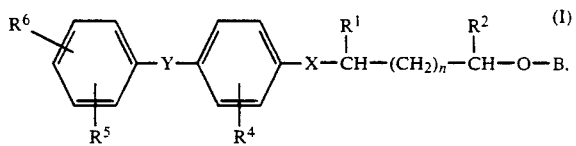

where X and Y are O, S, SO, SO$_2$ or CH$_2$, B is N-pyrazolyl or N-1,2,4-triazolyl of the formulae Ba and Bb respectively

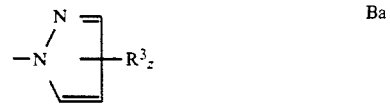

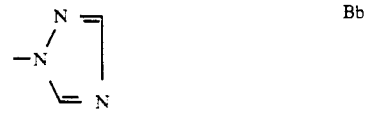

R$^1$ and R$^2$ are hydrogen or C$_1$-C$_3$-alkyl, R$^3$ is hydrogen, halogen or C$_1$-C$_3$-alkyl, z is 1, 2 or 3, R$^4$, R$^5$ and R$^6$ are hydrogen, halogen, C$_1$-C$_4$-alkyl, C$_1$-C$_4$-alkoxy, C$_1$-C$_4$-haloalkyl or C$_1$-C$_4$-haloalkoxy, and n is 0, 1 or 2, and methods of combating pests.

5 Claims, No Drawings

SUBSTITUTED N-HYDROXYPYRAZOLES AND N-HYDROXY-TRIAZOLES FOR CONTROLLING PESTS

This application is a continuation of application Ser. No. 07/482,909, filed on Feb. 22, 1990, now abandoned.

The present invention relates to novel substituted N-hydroxypyrazoles or N-hydroxytriazoles of the general formula I

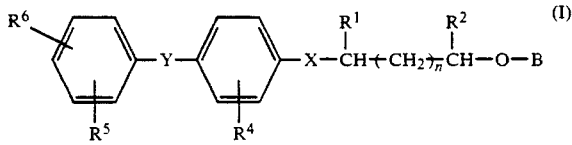

where
X and Y are O, S, SO, $SO_2$ or $CH_2$, B
is N-pyrazolyl or N-1,2,4-triazolyl of the formulae Ba and Bb respectively

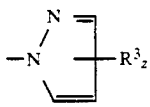

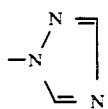

$R^1$ and $R^2$ are hydrogen or $C_1$-$C_3$-alkyl,
$R^3$ is hydrogen, halogen or $C_1$-$C_3$-alkyl,
Z is 1, 2 or 3,
$R^4$, $R^5$ and $R^6$ are hydrogen, halogen, $C_1$-$C_4$-alkyl, $C_1$-$C_4$-alkoxy, $C_1$-$C_4$-haloalkyl or $C_1$-$C_4$-haloalkoxy, is 0, 1 or 2.

The present invention also relates to agents for controlling pests which contain compounds I and to a method for controlling pests.

GB-A 2 115 812 discloses certain O-substituted oximes. However, the insecticidal effect of the compounds described therein is unsatisfactory. The insecticidal effect of the (p-phenoxyphenoxy)methylpyrazoles described in EP-A 289 919 (DE-A 37 14 709) is not always satisfactory either under certain conditions, e.g., low application rates.

The object of the present invention was to provide novel insecticidal compounds which are based on N-hydroxypyrazoles or -triazoles and which have effects superior to those of known compounds.

Accordingly, we have found that the substituted N-hydroxypyrazoles and N-hydroxytriazoles of the formula I defined in the introduction are outstandingly suitable for controlling pests. The substituted N-hydroxypyrazoles and -triazoles I according to the invention are prepared by reacting compounds of the formula II

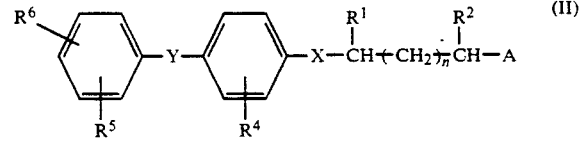

where A is a nucleophilically displaceable leaving group, with an N-hydroxypyrazole of the formula III

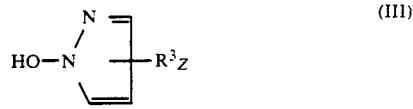

or an N-hydroxytriazole of the formula IV

in the presence of a base or directly with the alcoholate.

The reaction can take place from −20 to 250° C., preferably from 20° to 120° C., in accordance with the following equation:

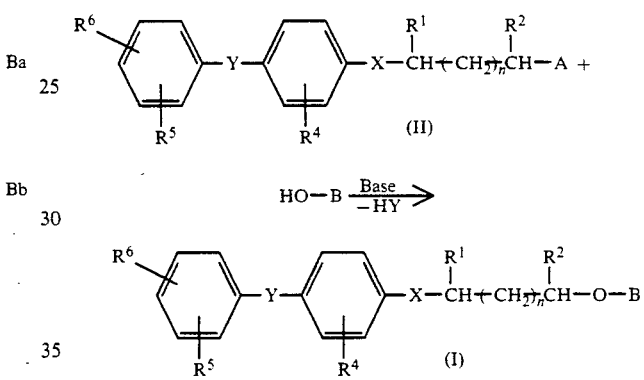

A in the above equation is a conventional leaving group such as a sulfonic acid residue or a halogen. Preferred sulfonic acid residues are methanesulfonyl, trifluoromethanesulfonyl and p-toluenesulfonyl, and preferred halogens are chlorine and bromine; chlorine is particularly preferred.

It is usual to add a base, in an amount which is at least equivalent to III, to II and/or III, but it can also be used in excess or as solvent. Examples of suitable bases are hydroxides of alkali metals and alkaline earth metals such as sodium hydroxide, potassium hydroxide and calcium hydroxide; alcoholates of alkali metals and alkaline earth metals such as sodium methylate, sodium ethylate, calcium methylate or potassium tert-butylate; alkali metal or alkaline earth metal hydrides such as sodium hydride, potassium hydride or calcium hydride; alkali metal or alkaline earth metal carbonates such as sodium carbonate, potassium carbonate or calcium carbonate; aliphatic amines such as dimethylamine, triethylamine or diisopropylamine; heterocyclic amines such as piperidine, piperazine or pyrrolidine; aromatic amines such as pyridine or pyrrole and possibly also alkyllithium compounds such as n-butyllithium.

To prepare the compound I according to the invention by the method described above the starting materials are normally employed in the stoichiometric ratio. However, in some cases an excess of one or the other may be advantageous.

The reaction is expediently carried out in a solvent or diluent. Suitable examples of these are aliphatic hydrocarbons such as n-pentane, n-hexane, the mixture of hexane isomers, and petroleum ether; aromatic hydrocarbons such as benzene, toluene, the xylenes and mixtures of isomers thereof; alcohols such as methanol, ethanol, n-propanol and isopropanol; ethers such as diethyl ether, di-n-butyl ether, methyl tert-butyl ether, tetrahydrofuran and dioxane; ketones such as acetone, methyl ethyl ketone and methyl isopropyl ketone; nitriles such as acetonitrile and propionitrile; aprotic dipolar solvents such as dimethylformamide, dimethyl sulfoxide or pyridine. It is also possible to use mixtures of these substances as solvents and diluents.

The reaction rates are usually sufficient above $-20°$ C. 120° C. should not in general be exceeded. Since the reactions evolve heat in some cases, it may be advantageous to provide means for cooling.

The reaction mixtures are worked up in a conventional manner, eg. by adding water, separating the phases and column chromatography. Some of the novel compounds of the formula I result in the form of colorless or pale brown viscous oils from which remaining volatiles can be removed by lengthy gentle heating under reduced pressure ("incipient distillation") and which can be purified in this way. If the compounds of the formula I are obtained as crystals, they can be purified by recrystallization.

The required intermediates II are disclosed in the literature and can be prepared, for example, by the process described in GB-A 2 115 812 as shown in the diagram below:

Route 1:

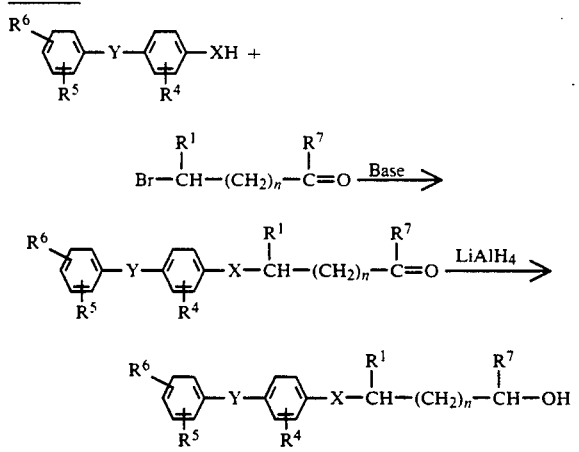

where $R^1$, $R^2$, $R^4$, $R^5$, $R^6$, X, Y and n have the meanings defined above, and $R^7$ is $-O-C_1-C_3$-alkyl when $R^2$ is hydrogen, and is the $C_1-C_3$-alkyl when $R^2$ is $C_1-C_3$-alkyl.

The hydroxyl group obtained as shown above can be converted in a conventional manner into other nucleophilically displaceable leaving groups, e.g., by reaction with phosphorus tribromide.

If A in starting material II is halogen, it is also possible to use the following route 2 for the preparation:

Route 2:

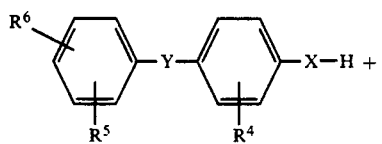

-continued

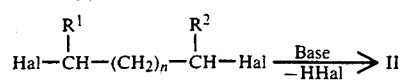

with A = halogen
$R^1$, $R^2$, $R^4$-$R^6$, X, Y and n have the above-mentioned meanings, and Hal is halogen, eg. bromine or chlorine.

The starting compounds used for both routes are known or can be prepared in a conventional manner (see, eg. Angew. Chem. 52 (1938) 915 or Japanese Patent Publication No. 62033/1980).

To prepare the N-hydroxypyrazoles of the formula III required as starting compounds, pyrazoles of the general formula V are converted into their metal salts of the general formula VI (Me is a cation of an alkali metal) in a conventional manner using an alkali metal hydroxide, hydride or carbonate The metal salts of the formula VI are then reacted with dibenzoyl peroxide in an inert organic solvent (eg. tetrahydrofuran) or in a two-phase system (eg. toluene/water), in the presence or absence of a phase transfer catalyst (eg. benzyltriethylammonium chloride). The reaction is generally carried out at from 0° to 60° C.

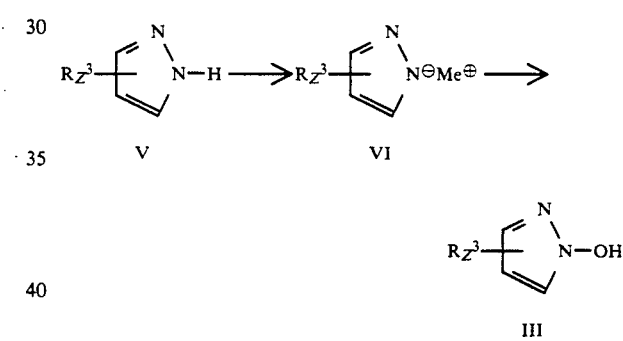

An alternative procedure is to react an alkali metal salt of the general formula VI with an aliphatic or aromatic peroxocarboxylic acid at from $-5°$ C. to 60° C.. The reaction can be carried out in water as solvent or in a two-phase system composed of water and an inert organic solvent which is immiscible with water (eg. toluene), in the presence or absence of a suitable phase transfer catalyst (eg. benzyltriethylammonium chloride). The peroxocarboxylic acid can be prepared from $H_2O_2$ and a carbonyl halide or anhydride in the reaction mixture before the reaction, or be used in the form of an alkali metal or alkaline earth metal salt.

Some of the N-hydroxypyrazoles are known or can be prepared by the process described in US 4 492 689.

N-Hydroxytriazole can be prepared by the process described in the older German Application P 39 00 347.7. This entails 1H-1,2,4-triazole VII being reacted with a peroxo compound, eg. hydrogen peroxide, at from $-20°$ C. to $+150°$ C. It is possible initially to add an agent which converts the 1H-triazole into the salt VII, The reaction is shown in the diagram below, where Me is a metal, eg. alkali metal:

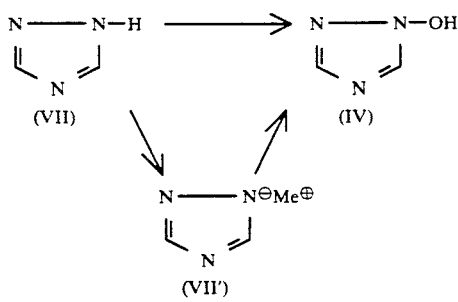

Where the 1H-1,2,4-triazole VII is reacted with compounds having peroxo groups but without addition of a salt-forming agent, the process is as follows: 1 to 3 mole equivalents of 1H-1,2,4-triazole VII are mixed, in a solvent such as water, water/acetone mixture, tetrahydrofuran, diglyme, methylene chloride or chloroform, with 1 mole equivalent of a peroxocarboxylic acid, preferably m-chloroperbenzoic acid. The reaction is carried out at from 0° to 50° C., preferably at room temperature.

Where the 1H-1,2,4-triazole is reacted with compounds having peroxo groups and with addition of a salt-forming agent, the process is as follows:

1 to 10 mole equivalents of 1H-1,2,4-triazole VII are metalated, in an inert solvent such as diglyme, tetrahydrofuran or diethyl ether, with an organometallic compound, a suspension of an alkali metal or a hydride, and then 1 mole equivalent of dibenzoyl peroxide is added. The mixture is stirred at room temperature for several days.

b) 1 to 3 mole equivalents of 1H-1,2,4-triazole VII are metalated, in water, with a hydroxide, a carbonate or a bicarbonate, and then 1 mole equivalent of peroxo carboxylic acid is added, and the mixture is stirred overnight. It is also possible to use an alkali metal or alkaline earth metal salt of the peroxocarboxylic acid in place of the acid, and to add it in solid form, for example.

Suitable salt-forming agents are organometallic compounds, e.g. metal alkyls such as n-butyllithium, tert-butyllithium and methyllithium, metal aryls such as phenyllithium, suspensions of alkali metals such as sodium in toluene or potassium in toluene, hydrides, eg. alkali metal hydrides such as lithium hydride, sodium hydride and potassium hydride, alkaline earth metal hydrides such as calcium hydride, preferably sodium hydride, hydroxides, eg. alkali metal hydroxides such as lithium hydroxide, sodium hydroxide and potassium hydroxide, alkaline earth metal hydroxides such as calcium hydroxide and magnesium hydroxide, carbonates, eg. alkali metal carbonates such as lithium carbonate, sodium carbonate and potassium carbonate, alkaline earth metal carbonates such as calcium carbonate and magnesium carbonate, and bicarbonates, e.g. sodium bicarbonate.

It is possible and preferable to carry out these reactions in the presence of a solvent. Suitable when organometallic compounds or hydrides are used are ethers such as diethyl ether, methyl butyl ether, tetrahydrofuran and dioxane, glycol ethers such as diglyme and triglyme, aliphatic hydrocarbons such as pentane, hexane, petroleum ether and cyclohexane, aromatic hydrocarbons such as benzene, toluene and the xylenes, or mixtures thereof.

Suitable when hydroxides, carbonates or bicarbonates are used are water, alcohols such as methanol, ethanol, n-propanol, iso-propanol and the butanols, ketones such as acetone and diethyl ketone, or mixtures thereof, preferably water.

Suitable compounds having peroxo groups are hydrogen peroxide or organic peroxides, e.g. dialkyl peroxides, alkyl aryl peroxides, diaryl peroxides, diacyl peroxides such as diacetyl peroxide, dipropionyl peroxide and dibenzoyl peroxide, preferably dibenzoyl peroxide; peroxo acids, e.g. peroxosulfonic acids such as p-tolueneperoxosulfonic acid, benzeneperoxosulfonic acid, p-bromobenzeneperoxosulfonic acid and methaneperoxosulfonic acid, preferably p-tolueneperoxosulfonic acid, peroxocarboxylic acids such as peroxoacetic acid, peroxobenzoic acid, m-chloroperbenzoic acid, peroxopropionic acid, peroxobutyric acid, peroxomaleic acid, monoperoxosuccinic acid and monoperoxophthalic acid, preferably monoperoxophthalic acid.

The specific meanings of the substituents in the formula I are as follows:

X and Y are O, S, SO, $SO_2$ or $CH_2$, preferably O and S, particularly preferably O, $R^1$ and $R^2$ are hydrogen, $C_1$-$C_3$-alkyl such as methyl, ethyl, propyl or i-propyl, preferably hydrogen and $C_1$-$C_2$-alkyl, particularly preferably hydrogen and methyl, $R^3$ is hydrogen, halogen or $C_1$-$C_3$-alkyl as specified for $R^1$, preferably hydrogen, chlorine and bromine, particularly preferably hydrogen, methyl and chlorine, $R^4$, $R^5$ and $R^6$ are hydrogen, halogen, particularly preferably hydrogen, chlorine, bromine and fluorine, $C_1$-$C_4$-alkyl, preferably $C_1$-$C_3$-alkyl, particularly preferably methyl, ethyl and i-propyl, $C_1$-$C_4$-alkoxy such as methoxy, ethoxy, propoxy or butoxy, preferably methoxy and ethoxy, $C_1$-$C_4$-haloalkyl, e.g. fluoro- or chloroalkyl, preferably $C_1$-$C_2$-fluoroalkyl, particularly preferably trifluoromethyl, $C_1$-$C_4$-haloalkoxy, preferably $C_1$-$C_3$-fluoralkoxy, particularly preferably difluoromethoxy, trifluoromethoxy or 1,1,2,2-tetrafluoroethoxy, n is 0, 1 or 2, preferably 0 and 1, particularly preferably 0, z is 1, 2 or 3, preferably 1 and 2, and monosubstituted (z=1) or unsubstituted pyrazoles are particularly preferred.

The compounds I according to the invention can contain one or more centers of asymmetry. The present invention includes all possible stereoisomers such as diastereomers and enantiomers as well as all mixtures of diastereomers and enantiomers.

The substituted N-hydroxypyrazoles and N-hydroxytriazoles of the formula I are suitable for effectively combating pests such as insects, arachnids and nematodes. They may be used as pesticides in crop protection and in the hygiene, stores protection and veterinary sectors.

Examples of injurious insects belonging to the Lepidoptera order are *Agrotis ypsilon, Agrotis segetum, Alabama argillacea, Anticarsia gemmatalis, Argyresthia conjugella, Autographa gamma, supalus piniarius, cacoecia murinana, Capua reticulana, Cheimatobia brumata, Choristoneura fumiferana, Choristoneura occidentalis, Cirphis unipuncta, Cydia pomonella, Oendrolimus pini, oiaphania nitidalis, Oiatraea grandiosella, Earias insulana, Elasmopalpus lignosellus, Eupoecilia ambiguella, Evetria bouliana, Feltia subterranea, Galleria mellonella, Gra-*

*pholita funebrana, Graphoiita molesta Heliothis armigera, Heliothis virescens, Heliothis zea, Hellula undalis, Hibernla defoliaria, Hyphantria cunea, Hyponomeuta malinellus, Keifferia lycopersicella, Lambdina fiscellaria, Laphygma exigua, Leucoptera coffeella, Leucoptera scltella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis.*

Examples from the Coleoptera order are *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, conoderus vespertinus, crioceris asparagi, Oiabrotica longicornis, Oiabrotica* 12-punctata, *Oiabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Ortiorrhynchus ovatus, Phaedon cochleariae, Phyllotreta chrysocephala, Phyllophaga sp,, Phyllopertha horticola, Phyllotreta nemorum, Phyllotreta striolata, Popillia japonica, Sitona lineatus* and *Sitophilus granaria.*

Examples from the Diptera order are *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Oacus cucurbitae, Oacus oieae, Oasineura brassicae Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria Pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa.*

Examples from the Thysanoptera order are *Frankliniella fusca, Frankliniella occidentalis, Frankliniella tritici, Scirtothrips citri, Thrips oryzae, Thrips palmi* and *Thrips tabaci.*

Examples from the Hymenoptera order are *Athalia rosae Atta cephalotes, Atta sexdens, Atta texana, Hoplocampa minuta, Hoplocampa testudinea, Monomorium pharaonis, Solenopsis geminata* and *Solenopsis invicta.*

Examples from the Heteroptera order are *Acrosternum hilare, Blissus leucopterus, Cyrtopeltis notatus, Dysdercus cingulatus, Oysdercus intermedius, Eurygaster integriceps, Euchistus impictiventris, Leptoglossus phylloPus, Lygus lineolaris, Lygus Pratensis, Nezara viridula, Piesma quadrata, Solubea insularis* and *Thyanta perditor.*

Examples from the Homoptera order are *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, oreyfusia Piceae, Oyasphis radicola, Oysaulacorthum pseudosolani, Empoasca fabae, Macrosiphum avenae, Macrosiphum euphorbiae, Macrosiphon rosae, Megoura viciae, MetoPolophium dirhodum, Myzodes persicae, Myzus cerasi, Nilaparvata lugens, Pemphigus bursarius, Perkinsiella saccharicida, Phorodon humuli, Psyiia mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii.*

Examples from the lsoptera order are *Calo:ermes flavicollis, Leucotermes flavipes, Reticulitermes lucifugus* and *Termes natalensis.*

Examples from the Orthoptera order are *Acheta domestica, Blatta orientalis, Blattella germanica, Forficula auricularia, Gryllotalpa gryllotalpa, Locusta migratoria, Melanoplus birittatus, Melanoplus femur-rubrum, Melanoplus mexicanus, Melanoplus sanguinipes, Melanopius spretus, Nomadacris septemfasciata, Periplaneta americana, Schistocerca americana, Schlstocerca peregrina, Stauronotus maroccanus* and *Tachycines asynamorus.*

Examples from the Acarina order are *Amblyomma americanum, Amglyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, lxodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephaius appendiculatus, Rhipicephalus evertsi, Saccoptes scabiei, Tetranychus cinnabarinus, Tetranychus kanzawai, Tetranychus pacificus, Tetranychus telarius* and *Tetranychus urticae.*

Examples from the nematodes class are root-knot nematodes, e.g., *Meloidogyne hapla, Meloidogyne incognita* and *Meloidogyne javanica,* cyst-forming nematodes, e.g., *Globodera rostochiensis, Heterodera avenae, Hetrodera glycinae, Heterodera schachtii* and *Heterodera trifolii,* and stem and leaf eel-worms, e.g., *Belonolalmus longicaudatus, Ditylenchus destrucior, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying. atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols. isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding ±he active ingredients with a solid carrier.

Examples of formulations are given below.

I. 5 parts by weight of compound no. 1.1 is intimately mixed with 95 parts by weight of particulate kaolin. A dust is obtained containing 5% by weight of the active ingredient.

II. 30 parts by weight of compound no. 2.1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 1.2 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 2.2 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 2.5 is well mixed with 3 parts by 5 weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules. e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate. ammonium nitrate, and ureas, and vegetable products such as grain flours, bark meal, wood meal, and nutshell meal, cellulosic powders, etc.

The formulations generally contain from 0.1 to 95 and preferably 0.5 to 90% by weight of active ingredient.

The active ingredient concentrations in the finished formulations may vary over a wide range. Generally, they are from 0.0001 to 10, and preferably from 0.1 to 1%.

The active ingredients may also successfully be used in the ultra-low-volume ULV method, where it is possible to apply formulations containing more than 95 wt % of active ingredient, or even the active ingredient without additives.

In the open, the amount of active ingredient applied is for example from 0.01 to 10, particularly from 0.05 to 2, kg/ha.

There may be added to the active ingredients (if desired, immediately before use (tankmix)) oils of various types, herbicides, fungicides, other pesticides and bactericides. These agents may be added to the active ingredients according to the invention in a weight ratio of from 1:10 to 10:1.

MANUFACTURING EXAMPLES

A) Substituted N-hydroxypyrazoles

N-[Z-(4-phenoxyphenoxy-ethoxy]-pyrazole (Ex. no. 1.1 in Table 1 below)

While cooling and at 0° C. a solution of 1.0 g of N-hydroxypyrazole in 10 ml of dimethylformamide is dripped into a suspension of 0.3 g of sodium hydride in 10 ml of dimethylformamide. The mixture is stirred for a further hour, after which a solution of 4.7 g of 2-(4-phenoxy-phenoxy-ethyl-p-toluenesulfonate in 50 liters of dimethylformamide is added. The reaction batch is stirred for 12 hours at room temperature and then poured into 250 ml of ice water. The mixture is extracted three times with methyl tert-butyl ether, and the combined extracts are washed with 1N sodium hydroxide solution and then with water. The organic phase is dried with sodium sulfate, the solvent is stripped off under reduced pressure and the residue is chromatographed over silica gel using toluene as developer; there is obtained 2.7 g of N-[12-4-phenoxyphenoxy-ethoxy]-pyrazole of melting point 83°–85° C.

TABLE 1

$$R^6\text{-}\underset{R^5}{\text{Ar}}\text{-}Y\text{-}\underset{R^4}{\text{Ar}}\text{-}X\text{-}\overset{R^1}{C}H\text{-}(CH_2)_n\text{-}\overset{R^2}{C}H\text{-}O\text{-}N\text{=}\underset{}{\text{ring}}\text{-}R^3Z$$

| No. | $R^1$ | $R^2$ | $R^3$ | $R^4$ | $R^5$ | $R^6$ | Y | X | n | Phys. data mp: (°C.), IR: (cm$^{-1}$) |
|---|---|---|---|---|---|---|---|---|---|---|
| 1.1 | H | H | H | H | H | H | O | O | 0 | mp: 83–85 |
| 1.2 | H | H | 4-Cl | H | H | H | O | O | 0 | mp: 63–65 |
| 1.3 | H | H | 4-CH$_3$ | H | H | H | O | O | 0 | mp: 52–56 |
| 1.4 | H | H | H | H | H | H | O | O | 1 | IR: 1588, 1504, 1489, 1474, 1222, 1197 |
| 1.5 | H | H | H | H | 3-F | H | O | O | 0 | mp: 48–54 |
| 1.6 | H | H | H | H | 4-F | H | O | O | 0 | mp: 70 |
| 1.7 | H | H | H | H | 2-F | H | O | O | 0 | |
| 1.8 | H | H | H | H | 3-Cl | H | O | O | 0 | mp: 60–64 |
| 1.9 | H | H | H | H | 3-Br | H | O | O | 0 | mp: 57–61 |
| 1.10 | H | H | H | H | 3-CH$_3$ | H | O | O | 0 | IR: 1610, 1585, 1503, 1486, 1241, 1209 |
| 1.11 | H | H | H | H | 3-C$_2$H$_5$ | H | O | O | 0 | IR: 1608, 1583, 1504, 1486, 1236, 1209 |
| 1.12 | H | H | H | H | 3-OCH$_3$ | H | O | O | 0 | IR: 1603, 1590, 1503, 1488, 1210 |
| 1.13 | H | H | H | H | 3-CF$_3$ | H | O | O | 0 | mp: 61–62 |
| 1.14 | H | H | H | H | 3-F | 5-F | O | O | 0 | |
| 1.15 | H | H | H | H | 3-F | 4-F | O | O | 0 | |
| 1.16 | H | H | H | 3-F | H | H | O | O | 0 | mp: 68–71 |
| 1.17 | H | CH$_3$ | H | H | H | H | O | O | 0 | IR: 1589, 1505, 1490, 1233 |
| 1.18 | H | CH$_3$ | H | H | 3-F | H | O | O | 0 | IR: 1614, 1600, 1504, 1485, 1206 |
| 1.19 | H | CH$_3$ | H | H | 4-F | H | O | O | 0 | IR: 1508, 1497, 1235, 1207 |
| 1.20 | H | CH$_3$ | H | H | 2-F | H | O | O | 0 | |
| 1.21 | H | CH$_3$ | H | H | 3-Cl | H | O | O | 0 | IR: 1589, 1504, 1472, 1225 |
| 1.22 | H | CH$_3$ | H | H | 3-Br | H | O | O | 0 | IR: 1584, 1503, 1470, 1222 |
| 1.23 | H | CH$_3$ | H | H | 3-CH$_3$ | H | O | O | 0 | |
| 1.24 | H | CH$_3$ | H | H | 3-C$_2$H$_5$ | H | O | O | 0 | IR: 1504, 1486, 1234, 1209 |
| 1.25 | H | CH$_3$ | H | H | 3-OCH$_3$ | H | O | O | 0 | |
| 1.26 | H | CH$_3$ | H | H | 3-CF$_3$ | H | O | O | 0 | IR: 1594, 1504, 1492, 1450, 1329 |
| 1.27 | H | CH$_3$ | H | H | 3-F | 5-F | O | O | 0 | IR: 1626, 1601, 1504, 1466, 1208 |
| 1.28 | H | CH$_3$ | H | H | 3-F | 4-F | O | O | 0 | |
| 1.29 | H | CH$_3$ | H | 3-F | H | H | O | O | 0 | |
| 1.30 | H | (S)-CH$_3$ | H | H | H | H | O | O | 0 | |
| 1.31 | H | (R)-CH$_3$ | H | H | H | H | O | O | 0 | |
| 1.32 | CH$_3$ | H | H | H | H | H | O | O | 0 | IR: 1588, 1502, 1489, 1219 |
| 1.33 | CH$_3$ | H | H | H | 3-F | H | O | O | 0 | mp: 54–55 |
| 1.34 | CH$_3$ | H | H | H | 4-F | H | O | O | 0 | IR: 1505, 1495, 1231, 1206 |
| 1.35 | CH$_3$ | H | H | H | 2-F | H | O | O | 0 | |
| 1.36 | CH$_3$ | H | H | H | 3-Cl | H | O | O | 0 | IR: 1589, 1501, 1472, 1222 |
| 1.37 | CH$_3$ | H | H | H | 3-Br | H | O | O | 0 | |
| 1.38 | CH$_3$ | H | H | H | 3-CH$_3$ | H | O | O | 0 | |
| 1.39 | CH$_3$ | H | H | H | 3-C$_2$H$_5$ | H | O | O | 0 | |
| 1.40 | CH$_3$ | H | 4-H | H | 3-OCH$_3$ | H | O | O | 0 | |
| 1.41 | CH$_3$ | H | 4-H | H | 3-CF$_3$ | H | O | O | 0 | |
| 1.42 | CH$_3$ | H | 4-H | H | 3-F | 5-F | O | O | 0 | |
| 1.43 | CH$_3$ | H | 4-H | 3-F | H | H | O | O | 0 | |
| 1.44 | (S)-CH$_3$ | H | 4-H | H | H | H | O | O | 0 | |
| 1.45 | (R)-CH$_3$ | H | 4-H | H | H | H | O | O | 0 | |
| 1.46 | H | CH$_3$ | 4-Cl | H | H | H | O | O | 0 | |
| 1.47 | H | CH$_3$ | 4-Cl | H | 3-F | H | O | O | 0 | |
| 1.48 | H | CH$_3$ | 4-Cl | H | 4-F | H | O | O | 0 | |
| 1.49 | H | CH$_3$ | 4-Cl | H | 2-F | H | O | O | 0 | |
| 1.50 | H | CH$_3$ | 4-Cl | H | 3-Cl | H | O | O | 0 | |
| 1.51 | H | CH$_3$ | 4-Cl | H | 3-Br | H | O | O | 0 | IR: 1584, 1502, 1470, 1222 |
| 1.52 | H | CH$_3$ | 4-Cl | H | 3-CH$_3$ | H | O | O | 0 | |
| 1.53 | H | CH$_3$ | 4-Cl | H | 3-C$_2$H$_5$ | H | O | O | 0 | |
| 1.54 | H | CH$_3$ | 4-Cl | H | 3-OCH$_3$ | H | O | O | 0 | |
| 1.55 | H | CH$_3$ | 4-Cl | H | 3-CF$_3$ | H | O | O | 0 | |
| 1.56 | H | CH$_3$ | 4-Cl | H | 3-F | 5-F | O | O | 0 | |
| 1.57 | H | CH$_3$ | 4-Cl | H | 3-F | 4-F | O | O | 0 | |
| 1.58 | H | CH$_3$ | 4-Cl | 3-F | H | H | O | O | 0 | |
| 1.59 | CH$_3$ | H | 4-Cl | H | H | H | O | O | 0 | |
| 1.60 | CH$_3$ | H | 4-Cl | H | 3-F | H | O | O | 0 | |
| 1.61 | CH$_3$ | H | 4-Cl | H | 4-F | H | O | O | 0 | |
| 1.62 | CH$_3$ | H | 4-Cl | H | 2-F | H | O | O | 0 | |
| 1.63 | CH$_3$ | H | 4-Cl | H | 3-Cl | H | O | O | 0 | |
| 1.64 | CH$_3$ | H | 4-Cl | H | 3-Br | H | O | O | 0 | |
| 1.65 | CH$_3$ | H | 4-Cl | H | 3-CH$_3$ | H | O | O | 0 | |
| 1.66 | CH$_3$ | H | 4-Cl | H | 3-C$_2$H$_5$ | H | O | O | 0 | |
| 1.67 | CH$_3$ | H | 4-Cl | H | 3-OCH$_3$ | H | O | O | 0 | |
| 1.68 | CH$_3$ | H | 4-Cl | H | 3-CF$_3$ | H | O | O | 0 | |
| 1.69 | CH$_3$ | H | 4-Cl | H | 3-F | 5-F | O | O | 0 | |
| 1.70 | CH$_3$ | H | 4-Cl | 3-F | H | H | O | O | 0 | |
| 1.71 | (S)-CH$_3$ | H | 4-Cl | H | H | H | O | O | 0 | |
| 1.72 | (R)-CH$_3$ | H | 4-Cl | H | H | H | O | O | 0 | |

TABLE 1-continued

Structure:
R⁶—[phenyl(R⁵)]—Y—[phenyl(R⁴)]—X—CH(R¹)—(CH₂)ₙ—CH(R²)—O—N(triazole)—R³z

| No. | R¹ | R² | R³ | R⁴ | R⁵ | R⁶ | Y | X | n | Phys. data mp: (°C.), IR: (cm⁻¹) |
|---|---|---|---|---|---|---|---|---|---|---|
| 1.73 | H | CH₃ | 4-CH₃ | H | H | H | O | O | 0 | IR: 1589, 1504, 1489, 1223 |
| 1.74 | H | CH₃ | 4-CH₃ | H | 3-F | H | O | O | 0 | |
| 1.75 | H | CH₃ | 4-CH₃ | H | 4-F | H | O | O | 0 | IR: 1500, 1222, 1212 |
| 1.76 | H | CH₃ | 4-CH₃ | H | 2-F | H | O | O | 0 | |
| 1.77 | H | CH₃ | 4-CH₃ | H | 3-Cl | H | O | O | 0 | |
| 1.78 | H | CH₃ | 4-CH₃ | H | 3-Br | H | O | O | 0 | |
| 1.79 | H | CH₃ | 4-CH₃ | H | 3-CH₃ | H | O | O | 0 | |
| 1.80 | H | CH₃ | 4-CH₃ | H | 3-C₂H₅ | H | O | O | 0 | IR: 1589, 1503, 1485, 1235, 1208 |
| 1.81 | H | CH₃ | 4-CH₃ | H | 3-OCH₃ | H | O | O | 0 | |
| 1.82 | H | CH₃ | 4-CH₃ | H | 3-CF₃ | H | O | O | 0 | |
| 1.83 | H | CH₃ | 4-CH₃ | H | 3-F | 5-F | O | O | 0 | |
| 1.84 | H | CH₃ | 4-CH₃ | 3-F | H | H | O | O | 0 | |
| 1.85 | H | (S)-CH₃ | 4-CH₃ | H | H | H | O | O | 0 | |
| 1.86 | H | (R)-CH₃ | 4-CH₃ | H | H | H | O | O | 0 | |
| 1.87 | CH₃ | H | 4-CH₃ | H | H | H | O | O | 0 | IR: 1588, 1502, 1489, 1219 |
| 1.88 | CH₃ | H | 4-CH₃ | H | 3-F | H | O | O | 0 | |
| 1.89 | CH₃ | H | 4-CH₃ | H | 4-F | H | O | O | 0 | IR: 1506, 1495, 1233, 1207 |
| 1.90 | CH₃ | H | 4-CH₃ | H | 2-F | H | O | O | 0 | |
| 1.91 | CH₃ | H | 4-CH₃ | H | 3-Cl | H | O | O | 0 | |
| 1.92 | CH₃ | H | 4-CH₃ | H | 3-Br | H | O | O | 0 | |
| 1.93 | CH₃ | H | 4-CH₃ | H | 3-CH₃ | H | O | O | 0 | |
| 1.94 | CH₃ | H | 4-CH₃ | H | 3-C₂H₅ | H | O | O | 0 | |
| 1.95 | CH₃ | H | 4-CH₃ | H | 3-OCH₃ | H | O | O | 0 | |
| 1.96 | CH₃ | H | 4-CH₃ | H | 3-CF₃ | H | O | O | 0 | |
| 1.97 | CH₃ | H | 4-CH₃ | H | 3-F | 5-F | O | O | 0 | |
| 1.98 | CH₃ | H | 4-CH₃ | 3-F | H | H | O | O | 0 | |
| 1.99 | (S)-CH₃ | H | 4-CH₃ | H | H | H | O | O | 0 | |
| 1.100 | (R)-CH₃ | H | 4-CH₃ | H | H | H | O | O | 0 | |
| 1.101 | H | H | 4-H | H | H | H | CH₂ | O | 0 | |
| 1.102 | H | H | 4-H | H | H | H | S | O | 0 | |
| 1.103 | H | H | 4-H | H | H | H | O | S | 0 | |
| 1.104 | H | H | 4-Cl | H | 3-F | H | O | O | 0 | mp: 59–61 |
| 1.105 | H | H | 4-Cl | H | 4-F | H | O | O | 0 | |
| 1.106 | H | H | 4-Cl | H | 2-F | H | O | O | 0 | |
| 1.107 | H | H | 4-Cl | H | 3-Cl | H | O | O | 0 | |
| 1.108 | H | H | 4-Cl | H | 3-Br | H | O | O | 0 | IR: 1580, 1504, 1388 |
| 1.109 | H | H | 4-Cl | H | 3-CH₃ | H | O | O | 0 | mp: 53–54 |
| 1.110 | H | H | 4-Cl | H | 3-C₂H₅ | H | O | O | 0 | IR: 1603, 1583, 1504, 1486, 1236, 1209 |
| 1.111 | H | H | 4-Cl | H | 3-OCH₃ | H | O | O | 0 | |
| 1.112 | H | H | 4-Cl | H | 3-CF₃ | H | O | O | 0 | IR: 1505, 1451, 1230, 1226 |
| 1.113 | H | H | 4-Cl | H | 3-F | 5-F | O | O | 0 | |
| 1.114 | H | H | 4-Cl | 3-F | H | H | O | O | 0 | |
| 1.115 | H | H | 4-CH₃ | H | 3-F | H | O | O | 0 | |
| 1.116 | H | H | 4-CH₃ | H | 2-F | H | O | O | 0 | |
| 1.117 | H | H | 4-CH₃ | H | 4-F | H | O | O | 0 | mp: 66–70 |
| 1.118 | H | H | 4-CH₃ | H | 3-Cl | H | O | O | 0 | IR: 1588, 1503, 1472, 1225 |
| 1.119 | H | H | 4-CH₃ | H | 3-Br | H | O | O | 0 | |
| 1.120 | H | H | 4-CH₃ | H | 3-CH₃ | H | O | O | 0 | |
| 1.121 | H | H | 4-CH₃ | H | 3-C₂H₅ | H | O | O | 0 | |
| 1.122 | H | H | 4-CH₃ | H | 3-OCH₃ | H | O | O | 0 | |
| 1.123 | H | H | 4-CH₃ | H | 3-CF₃ | H | O | O | 0 | |
| 1.124 | H | H | 4-CH₃ | H | 3-F | 5-F | O | O | 0 | |
| 1.125 | H | H | 4-CH₃ | 3-F | H | H | O | O | 0 | |

B) Substituted N-hydroxytriazoles

1-{2-[4-3-Chloro)-phenoxy-phenoxy]ethoxy}-1,2,4-triazole (Ex. no. 2.19 in Table 2 below)

While cooling with ice, a solution of 0.96 g 11.3 mmol) of 1-hydroxy-1,2,4-triazole in 10 cm³ of dimethylformamide is dripped into a suspension of 0.31 g (12.4 mmol) of sodium hydride in 3 cm³ of dimethylformamide. After stirring for 30 minutes, a solution of 3.9 g (11.3 mmol) of 2-[4-(3-chloro)-phenoxy-phenoxy]-ethyl-methylsulfonate in 20 cm³ of dimethylformamide is dripped in at 60° C., and then the mixture is stirred for 3 hours at 80° C. and for a further 14 hours at room temperature. Volatile constituents are then removed, the residue is taken up in about 100 cm³ of ethyl acetate, and the whole is washed with water, dried over sodium sulfate and evaporated down. A yellowish oil remains.

Yield: 2.9 g (77% of theory).

Infrared absorptions [cm⁻¹]: 1502, 1472, 1273, 1222, 1195, 1004, 907, 840, 680.

1H NMR spectrum (300 MHz in COCl₃; δ values in ppm against tetramethylsilane): 4.23 (2H,m,c), 4.71 (2H,m,c), 6.80–7.28 (8H,m), 7.8 (1H,s), 8.11 (1H,s).

TABLE 2

Substituted N-hydroxytriazoles I

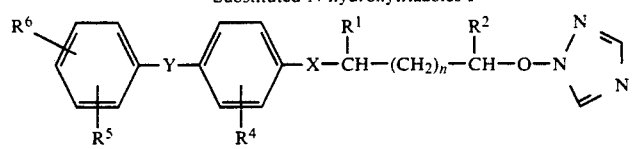

| No. | $R^1$ | $R^2$ | $R^4$ | $R^5$ | $R^6$ | X | Y | n | Phys. data mp: (°C.), IR(cm$^{-1}$) |
|---|---|---|---|---|---|---|---|---|---|
| 2.1 | H | H | H | H | H | O | O | 0 | mp: 66–67 |
| 2.2 | CH$_3$ | H | H | H | H | O | O | 0 | 1502, 1488, 1274, 1218, 1198, 1005, 870, 843, 681 |
| 2.3 | H | CH$_3$ | H | H | H | O | O | 0 | |
| 2.4 | H | H | H | 3-F | H | O | O | 0 | |
| 2.5 | CH$_3$ | H | H | 3-F | H | O | O | 0 | 1502, 1484, 1272, 1240, 1205, 1121, 1005, 960, 681 |
| 2.6 | H | CH$_3$ | H | 3-F | H | O | O | 0 | 1504, 1485, 1272, 1241, 1206, 1121, 1004, 960, 681 |
| 2.7 | H | H | H | 2-F | H | O | O | 0 | |
| 2.8 | CH$_3$ | H | H | 2-F | H | O | O | 0 | |
| 2.9 | H | CH$_3$ | H | 2-F | H | O | O | 0 | |
| 2.10 | H | H | H | 4-F | H | O | O | 0 | |
| 2.11 | CH$_3$ | H | H | 4-F | H | O | O | 0 | mp: 56–57 |
| 2.12 | H | CH$_3$ | H | 4-F | H | O | O | 0 | |
| 2.13 | H | H | 3-F | H | H | O | O | 0 | 1507, 1486, 1253, 1245, 1167, 976, 836, 763, 680 |
| 2.14 | CH$_3$ | H | 3-F | H | H | O | O | 0 | |
| 2.15 | H | CH$_3$ | 3-F | H | H | O | O | 0 | |
| 2.16 | H | H | 3-F | 3-F | H | O | O | 0 | |
| 2.17 | CH$_3$ | H | 3-F | 3-F | H | O | O | 0 | |
| 2.18 | H | CH$_3$ | 3-F | 3-F | H | O | O | 0 | |
| 2.19 | H | H | H | 3-Cl | H | O | O | 0 | 1502, 1472, 1273, 1222, 1195, 1004, 907, 840, 680 |
| 2.20 | CH$_3$ | H | H | 3-Cl | H | O | O | 0 | 1501, 1472, 1273, 1220, 1195, 1005, 907, 843, 681 |
| 2.21 | H | CH$_3$ | H | 3-Cl | H | O | O | 0 | |
| 2.22 | H | H | H | 2-Cl | H | O | O | 0 | |
| 2.23 | CH$_3$ | H | H | 2-Cl | H | O | O | 0 | |
| 2.24 | H | CH$_3$ | H | 2-Cl | H | O | O | 0 | |
| 2.25 | H | H | H | 4-Cl | H | O | O | 0 | |
| 2.26 | CH$_3$ | H | H | 4-Cl | H | O | O | 0 | |
| 2.27 | H | CH$_3$ | H | 4-Cl | H | O | O | 0 | |
| 2.28 | H | H | H | 3-Br | H | O | O | 0 | |
| 2.29 | CH$_3$ | H | H | 3-Br | H | O | O | 0 | |
| 2.30 | H | CH$_3$ | H | 3-Br | H | O | O | 0 | |
| 2.31 | H | H | H | 2-Br | H | O | O | 0 | |
| 2.32 | CH$_3$ | H | H | 2-Br | H | O | O | 0 | |
| 2.33 | H | CH$_3$ | H | 2-Br | H | O | O | 0 | |
| 2.34 | H | H | H | 4-Br | H | O | O | 0 | |
| 2.35 | CH$_3$ | H | H | 4-Br | H | O | O | 0 | |
| 2.36 | H | CH$_3$ | H | 4-Br | H | O | O | 0 | |
| 2.37 | H | H | H | 3-CH$_3$ | H | O | O | 0 | |
| 2.38 | CH$_3$ | H | H | 3-CH$_3$ | H | O | O | 0 | |
| 2.39 | H | CH$_3$ | H | 3-CH$_3$ | H | O | O | 0 | |
| 2.40 | H | H | H | 2-CH$_3$ | H | O | O | 0 | |
| 2.41 | CH$_3$ | H | H | 2-CH$_3$ | H | O | O | 0 | |
| 2.42 | H | CH$_3$ | H | 2-CH$_3$ | H | O | O | 0 | |
| 2.43 | H | H | H | 4-CH$_3$ | H | O | O | 0 | |
| 2.44 | CH$_3$ | H | H | 4-CH$_3$ | H | O | O | 0 | |
| 2.45 | H | CH$_3$ | H | 4-CH$_3$ | H | O | O | 0 | |
| 2.46 | H | H | H | 3-C$_2$H$_5$ | H | O | O | 0 | |
| 2.47 | CH$_3$ | H | H | 3-C$_2$H$_5$ | H | O | O | 0 | |
| 2.48 | H | CH$_3$ | H | 3-C$_2$H$_5$ | H | O | O | 0 | 1503, 1485, 1447, 1273, 1234, 1208, 1003, 917, 833, 682 |
| 2.49 | H | H | H | 2-C$_2$H$_5$ | H | O | O | 0 | |
| 2.50 | CH$_3$ | H | H | 2-C$_2$H$_5$ | H | O | O | 0 | |
| 2.51 | H | CH$_3$ | H | 2-C$_2$H$_5$ | H | O | O | 0 | |
| 2.52 | H | H | H | 3-i-C$_3$H$_7$ | H | O | O | 0 | |
| 2.53 | CH$_3$ | H | H | 3-i-C$_3$H$_7$ | H | O | O | 0 | |
| 2.54 | H | CH$_3$ | H | 3-i-C$_3$H$_7$ | H | O | O | 0 | |
| 2.55 | H | H | H | 3-i-C$_3$H$_7$ | H | O | O | 0 | |
| 2.56 | CH$_3$ | H | H | 3-i-C$_3$H$_7$ | H | O | O | 0 | |
| 2.57 | H | CH$_3$ | H | 3-i-C$_3$H$_7$ | H | O | O | 0 | |
| 2.58 | H | H | H | 3-i-C$_3$H$_7$ | H | O | O | 0 | |
| 2.59 | CH$_3$ | H | H | 3-i-C$_3$H$_7$ | H | O | O | 0 | |
| 2.60 | H | CH$_3$ | H | 3-i-C$_3$H$_7$ | H | O | O | 0 | |
| 2.61 | H | H | H | 3-OCH$_3$ | H | O | O | 0 | 1503, 1488, 1451, 1274, 1242, 1210, 1138, 682 |
| 2.62 | CH$_3$ | H | H | 3-OCH$_3$ | H | O | O | 0 | |
| 2.63 | H | CH$_3$ | H | 3-OCH$_3$ | H | O | O | 0 | |
| 2.64 | H | H | H | 2-OCH$_3$ | H | O | O | 0 | |
| 2.65 | CH$_3$ | H | H | 2-OCH$_3$ | H | O | O | 0 | |
| 2.66 | H | CH$_3$ | H | 2-OCH$_3$ | H | O | O | 0 | |
| 2.67 | H | H | H | 4-OCH$_3$ | H | O | O | 0 | |
| 2.68 | CH$_3$ | H | H | 4-OCH$_3$ | H | O | O | 0 | |
| 2.69 | H | CH$_3$ | H | 4-OCH$_3$ | H | O | O | 0 | |
| 2.70 | H | H | H | 3-OC$_2$H$_5$ | H | O | O | 0 | |
| 2.71 | CH$_3$ | H | H | 3-OC$_2$H$_5$ | H | O | O | 0 | |

TABLE 2-continued

Substituted N-hydroxytriazoles I $$R^6 - \text{(ring)}_{R^5} - Y - \text{(ring)}_{R^4} - X - \underset{R^1}{CH} - (CH_2)_n - \underset{R^2}{CH} - O - N \underset{N}{\overset{N}{\diagdown}} \quad (I)$$

| No. | R¹ | R² | R⁴ | R⁵ | R⁶ | X | Y | n | Phys. data mp: (°C.), IR(cm⁻¹) |
|---|---|---|---|---|---|---|---|---|---|
| 2.72 | H | CH₃ | H | 3-OC₂H₅ | H | O | O | 0 | |
| 2.73 | H | H | H | 2-OC₂H₅ | H | O | O | 0 | |
| 2.74 | CH₃ | H | H | 2-OC₂H₅ | H | O | O | 0 | |
| 2.75 | H | CH₃ | H | 2-OC₂H₅ | H | O | O | 0 | |
| 2.76 | H | H | H | 4-OC₂H₅ | H | O | O | 0 | |
| 2.77 | CH₃ | H | H | 4-OC₂H₅ | H | O | O | 0 | |
| 2.78 | H | CH₃ | H | 4-OC₂H₅ | H | O | O | 0 | |
| 2.79 | H | H | H | 3-CF₃ | H | O | O | 0 | |
| 2.80 | CH₃ | H | H | 3-CF₃ | H | O | O | 0 | |
| 2.81 | H | CH₃ | H | 3-CF₃ | H | O | O | 0 | |
| 2.82 | H | H | H | 2-CF₃ | H | O | O | 0 | |
| 2.83 | CH₃ | H | H | 2-CF₃ | H | O | O | 0 | |
| 2.84 | H | CH₃ | H | 2-CF₃ | H | O | O | 0 | |
| 2.85 | H | H | H | 4-CF₃ | H | O | O | 0 | |
| 2.86 | CH₃ | H | H | 4-CF₃ | H | O | O | 0 | |
| 2.87 | H | CH₃ | H | 4-CF₃ | H | O | O | 0 | |
| 2.88 | H | H | H | 3-OCF₃ | H | O | O | 0 | |
| 2.89 | CH₃ | H | H | 3-OCF₃ | H | O | O | 0 | |
| 2.90 | H | CH₃ | H | 3-OCF₃ | H | O | O | 0 | |
| 2.91 | H | H | H | 2-OCF₃ | H | O | O | 0 | |
| 2.92 | CH₃ | H | H | 2-OCF₃ | H | O | O | 0 | |
| 2.93 | H | CH₃ | H | 2-OCF₃ | H | O | O | 0 | |
| 2.94 | H | H | H | 4-OCF₃ | H | O | O | 0 | |
| 2.95 | CH₃ | H | H | 4-OCF₃ | H | O | O | 0 | |
| 2.96 | H | CH₃ | H | 4-OCF₃ | H | O | O | 0 | |
| 2.97 | H | H | H | 3-OCF₂CF₂H | H | O | O | 0 | |
| 2.98 | CH₃ | H | H | 3-OCF₂CF₂H | H | O | O | 0 | |
| 2.99 | H | CH₃ | H | 3-OCF₂CF₂H | H | O | O | 0 | |
| 2.100 | H | H | H | 2-OCF₂CF₂H | H | O | O | 0 | |
| 2.101 | CH₃ | H | H | 2-OCF₂CF₂H | H | O | O | 0 | |
| 2.102 | H | CH₃ | H | 2-OCF₂CF₂H | H | O | O | 0 | |
| 2.103 | H | H | H | 4-OCF₂CF₂H | H | O | O | 0 | |
| 2.104 | CH₃ | H | H | 4-OCF₂CF₂H | H | O | O | 0 | |
| 2.105 | H | CH₃ | H | 4-OCF₂CF₂H | H | O | O | 0 | |
| 2.106 | H | H | H | 3-F | 5-F | O | O | 0 | |
| 2.107 | CH₃ | H | H | 3-F | 5-F | O | O | 0 | |
| 2.108 | H | CH₃ | H | 3-F | 5-F | O | O | 0 | 1505, 1466, 1244, 1208, 1121, 1009, 995, 836 |
| 2.109 | H | H | 3-F | 3-F | 5-F | O | O | 0 | |
| 2.110 | CH₃ | H | 3-F | 3-F | 5-F | O | O | 0 | |
| 2.111 | H | CH₃ | 3-F | 3-F | 5-F | O | O | 0 | |

C) Manufacture of 1-hydroxy-1,2,4-triazole 103.5 g (1.5 mol) of 1-H-1,2.4-triazole is dissolved in 1344 g (12 mol) of 50% strength aqueous potassium hydroxide. While cooling with ice, 340 g (3 mol) of 30% strength H₂O₂ and—in portions—555 g (3.75 mol of phthalic anhydride are added and the mixture is stirred for 2 hours at room temperature 20° to 30° C. The mixture is then acidified to a pH of <1.5 with approx. 35% strength sulfuric acid, the precipitate formed is filtered off and the filtrate is investigated by quantitative HPLC. There is obtained 19 g (15%) of N-hydroxy-1,2,4-triazole, which is worked up in conventional manner; m.p. 132° C.

USE EXAMPLES

In the following examples, the action on pests of compounds according to the invention, or agents containing them, is compared with that of the following compound A disclosed in GB-A-2,115,812:

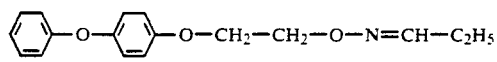

The purity of the substances was >95 %. The concentrations at which the investigated compounds exhibit 100% kill are the minimum concentrations. At least two experiments were carried out for each concentration.

The active ingredient was used as a 10% emulsion concentrate obtained by emulsifying the active ingredient in a mixture containing 70 wt % of cyclohexanone, 20 wt % of Nekanil ® LN ≙ Lutensol AP6, a spreader-sticker with an emulsifying and dispersing action based on ethoxylated alkylphenols and 10 wt % of Emulphor EL ® (an emulsifier based on ethoxylated fatty alcohols). The concentrations given in the examples were obtained by diluting the formulated active ingredient with water.

EXAMPLE A

Ovicidal action on *Oysdercus intermedius* (cotton stainer)

Pieces of double-sided adhesive tape (about 0.8 cm) were stuck to the top edge of plastic plant markers. 24 hours before commencement of the experiment, eggs of the cotton stainer contained in a vessel were attached to the adhesive strips by dipping the markers into the vessel. The eggs were then dipped for 5 seconds into aqueous formulations of the active ingredients and excess liquid was allowed to drip off onto filter paper, care being taken to prevent the eggs coming into contact with the paper.

The markers were then placed in plastic trays (adhesive strip at the top). Half a roll of absorbent cotton was moistened with water and placed in each beaker to prevent drying out, and the trays were covered with a glass plate. Assessment took place after 8 days control bugs hatched.

In this experiment, compounds nos. 1.1, 1.2, 1.5, 1.104, 2.1, 2.2, 2.6, 2.13 and 2.108 had a better action than comparative agent A, which was ineffective at a concentration of 1,000 ppm.

EXAMPLE B

Breeding experiment with *Musca domestica* (housefly)

The experiment was run in 100 ml plastic beakers. 25cm$^3$ of a dry feed mix (1 g of bran. 250 g of yeast powder and 35 g of fishmeal) was introduced into the beakers, the active ingredients were added together with 25 ml of a solution of milk and sugar (1 liter of milk and 42 cm$^3$ of liquid sugar) and the whole was mixed with a spatula. About 30 larvae in the first larvai stage were then placed in each beaker. Perforated lids were then placed on the beakers. The experiment was run until the flies hatched.

In this experiment, compounds nos. 1.1, 1.5, 1.8, 1.9, 1.13 and 1.104 had a better action than comparative agent A, which was ineffective at a concentration of 100 ppm.

EXAMPLE C

Breeding experiment with *Prodenia litura*

Breeding took place in 100 ml plastic beakers on about 50 ml of the standard nutrient medium (3.1 liters of water, 80 g of agar, 137 g of brewers' yeast, 515 g of corn meal, 130 g of wheat germ and conventional additives and vitamins), to which the active ingredients were carefully admixed while liquid. For each concentration, 5 caterpillars of the fourth larval stage were introduced into each beaker. The temperature was kept at 25° to 26° C. The experiment was monitored until the moths emerged. A sample was considered to be effective when giant larvae were produced.

In this experiment, compounds 1.1., 1.8 and 1.9 had a better action than comparative agent A.

We claim:

1. A substituted N-hydroxypyrazole of the formula

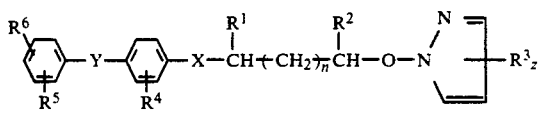

where X and Y are O, S, SO, SO$_2$ or CH$_2$, R$^1$ and R$^2$ are hydrogen or C$_1$–C$_3$-alkyl, R$^3$ is hydrogen, halogen or C$_1$–C$_3$-alkyl, z is 1, 2 or 3, R$^4$, R$^5$ and R$^6$ are hydrogen, halogen, C$_1$–C$_4$-alkyl, C$_1$–C$_4$-alkoxy, C$_1$–C$_4$-haloalkyl or C$_1$–C$_4$-haloalkoxy, and n is 0, 1 or 2.

2. A substituted N-hydroxypyrazole of the formula I as set forth in claim 1, where X and Y are oxygen and n is 0.

3. A composition containing an insecticidally, arachnidicidally or hematodicidally effective amount of a substituted N-hydroxypyrazole of the formula I as set forth in claim 1 and conventional carriers therefor.

4. A composition as set forth in claim 3, containing from 0.1 to 95 wt. % of the substituted N-hydroxypyrazole of the formula I.

5. A process for combating insects, arachnids and nematodes, wherein the insects, arachnids and nematodes and/or the areas and/or spaces to be kept free from insects, arachnids and nematodes are treated with an effective amount of a substituted N-hydroxypyrazole of the formula I as set forth in claim 1.

* * * * *

UNITED STATES PATENT AND TRADEMARK OFFICE
CERTIFICATE OF CORRECTION

PATENT NO. : 5,120,756
DATED : June 9, 1992
INVENTOR(S) : NEUBAUER et al.

It is certified that error appears in the above-identified patent and that said Letters Patent is hereby corrected as shown below:

Claim 3, column 20, line 28, "hematodicidally" should read --nematodicidally--.

This Certificate supersedes Certificate of Correction issued July 27, 1993.

Signed and Sealed this

Twenty-second Day of March, 1994

Attest:

BRUCE LEHMAN

Attesting Officer — Commissioner of Patents and Trademarks